United States Patent [19]

Diamandis

[11] Patent Number: 5,312,922

[45] Date of Patent: May 17, 1994

[54] EUROPIUM AND TERBIUM CHELATORS FOR TIME-RESOLVED FLUOROMETRIC ASSAYS

[75] Inventor: Eleftherios P. Diamandis, Toronto, Canada

[73] Assignee: Nordion International Inc., Kanata, Canada

[21] Appl. No.: 863,746

[22] Filed: Apr. 6, 1992

[51] Int. Cl.$^5$ .......................................... C07D 215/16
[52] U.S. Cl. .................... 546/156; 544/255; 544/302; 546/153; 546/155; 546/168
[58] Field of Search ............... 546/156, 155, 153, 168

[56] References Cited

FOREIGN PATENT DOCUMENTS

| | | |
|---|---|---|
| 171978 | 2/1986 | European Pat. Off. |
| 191575 | 8/1986 | European Pat. Off. |
| 201211 | 11/1986 | European Pat. Off. |
| 290269 | 5/1987 | European Pat. Off. |
| 86/01604 | 3/1986 | World Int. Prop. O. |

OTHER PUBLICATIONS

Christopoulos et al., "Enzymatically Amplified Time-Resolved Fluorescence Immunoassay with Terbium Chelates", *Analyt. Chem.*, vol. 64, pp. 342–346 (1992).

Diamandis et al., "Time-Resolved Fluorescence Using Europium Chelate 4,7-bis-(chlorosulfophenyl)1-,10--phenanthroline-2,9-dicarboxylic acid (BCPDA)", *J. Immunol. Meth.*, 112:43–52 (1988).

Evangelista et al., "Enzyme-Amplified Lanthanide Luminescence for Enzyme Detection in Bioanalytical Assays", *Anal. Biochem.*, v. 197, pp. 213–224 (1991).

Kallistratos, "Fluorescent Properties of Aromatic Complexes with Rare Earths and Other Elements of the IIIa-Group", *Chimika Chronika, New Series*, v. 11, pp. 249–266 (1982).

Khosravi et al., *Chem. Abst.*, 108:16385p (1988).

Papanastasiou-Diamandi et al., "Ultrasensitive Thyrotropin Immunoassay Based on Enzymatically Amplified Time-Resolved Fluorescence with Terbium Chelate", *Clinical Chem.*, vol. 38, No. 4, pp. 545–548 (1992).

*Primary Examiner*—C. Warren Ivy
*Assistant Examiner*—James H. Turnipseed
*Attorney, Agent, or Firm*—Banner, Birch, McKie & Beckett

[57] ABSTRACT

Fluorogenic chelators for $Eu^{3+}$ and $Tb^{3+}$ are provided, they form highly fluorescent complexes with $Eu^{3+}$ and $Tb^{3+}$. In all cases, the fluorescence observed was lanthanide-specific, long-lived and it was monitored by microsecond time-resolved fluorometry. The fluorogenic chelators could be quantified, in the presence of excess lanthanide, at levels $<10^{-8}$ mol/L. Two new fluorogenic chelators can form ternary complexes with $Eu^{3+}$ and $Tb^{3+}$, in the presence of EDTA. The structures of the identified chelators is such that enzyme substrates can be used for enzyme-labelled time-resolved fluorometric immunoassays. The chelator 4-methylumbelliferyl phosphate which forms fluorescent, long-lived complexes with $Eu^{3+}$, can be split by alkaline phosphatase to phosphate and 4-methylumbelli-ferone which does not form fluorescent complexes with $Eu^{3+}$. Highly sensitive immunoassays for thyrotropin and thyroxine in human serum are demonstrated.

4 Claims, 8 Drawing Sheets

EUROPIUM AND TERBIUM CHELATORS FOR TIME-RESOLVED FLUOROMETRIC ASSAYS

FIELD OF THE INVENTION

This invention relates to florescent lanthanide metal chelates.

BACKGROUND OF THE INVENTION

In order to facilitate discussion of known fluorescent entities, their application and the manner in which the fluorescent entities in this invention distinguish from known systems, reference will be made to several scientific articles throughout the specification. To facilitate such reference the articles have been listed by number as follows:

1. Diamandis, E. P. Clin. Biochem. 1988, 21, 139–150.
2. Diamandis, E. P. Clin. Chim. Acta. 1990, 194, 19–50.
3. Diamandis, E. P.; Christopoulos, T. K. Anal. Chem. 1990, 62, 11 49A-11 57A.
4. Soini, E.; Lovgren, T. CRC Crit. Rev. Anal. Chem. 1987, 18, 105–154.
5. Hemmila, I.; Dakubu, S.; Mukkala V. M.; Siitari, H.; Lovgren, T. Anal. Biochem. 137, 335–343.
6. Soini, E.; Kojola, H. Clin. Chem. 1983, 29, 15–68.
7. Evangelista, R. A.; Pollak, A.; Allore, B.; Templeton, E. F.; Morton, R. C.; Diamandis, E. P. Clin. Biochem. 1988, 21, 173–178.
8. Diamandis, E. P.; Morton, R. C.; J. Immunol. Method 1988, 12, 43–52.
9. Bailey, M. P.; Rocks, B. F.; Riley, C. Analyst 1984, 109, 1449–1450.
10. Oser, A.; Gollasius, M.; Valet, G. Anal. Biochem. 1990, 191, 295–301.
11. Hemmila, I.; I Hoittinen, S.; Pettersson, K.; Lovgren, T. Clin. Chem. 1987, 33, 2281–2283.
12. Sinha, A. P. B. Spectrosc. Inorg. Chem. 1971, 2, 255–265.
13. Kallistratos, G. Chimica Chronica New Series, 1982, 11, 249–266.
14. Diamandis, E. P.; Morton, R. C.; Reichstein, E.; Khosravi, M. J. Anal. Chem. 1989, 61, 48–53.
15. Morton, R. C.; Diamandis, E. P. Anal. Chem. 1990, 62, 1841–1845.
16. Diamandis, E. P. Clin. Chem. 1991, 37, 1486–1491.
17. Evangelists, R. A.; Pollak, A.; Gudgin-Templeton, E. F. Anal. Biochem. 1991, 197, 213–224.
18. Christopoulos, T. K.; Diamandis, E. P. Anal. Chem. 1992, (in press).
19. Papanastasiou-Diamandi, A.; Christopoulos, T. K.; Diamandis, E. P. Clin. Chem. 1992 (in press).
20. Papanastasiou-Diamandi, A.; Bhayana, V.; Diamandis, E. P. Ann. Clin. Biochem. 1989, 26, 238–243.

Fluorescent lanthanide metal chelates and in particular those for europium and terbium chelates have significant commercial application because of their use as labels in highly sensitive time-resolved fluorometric immunoassays (1–4). The first commercially available time-resolved fluorescence immunoassay system, Delfia ™ (available by Pharmacia-LKB, Sweden) uses $Eu^{3+}$ as immunological label (5,6). A second-generation time-resolved fluorometric immunoassay system, FIAgen ™ (available by CyberFluor Inc., Toronto, Canada, the applicant in this application) uses the europium chelator 4,7-bis (chlorosulfophenyl)-1,10-phenanthroline-2,9-dicarboxylic acid (BCPDA) as immunological label (7,8). These two systems, along with the principles of time-resolved fluorometry and its application to immunoassay and other bioanalytical techniques have been investigated in detail (1–4).

Recently, $Tb^{3+}$ and its chelates have been used as immunological and nucleic acid labels (9,10). In general, $Tb^{3+}$ is inferior to $Eu^{3+}$ in terms of detectability. However, $Eu^{3+}$ and $Tb^{3+}$ can be used simultaneously for dual analyte assays (11).

The mechanism of fluorescence of the $Eu^{3+}$ and $Tb^{3+}$ chelates has been described (1–4). These two ions, when excited by radiation, emit very weak metal-ion fluorescence which is not analytically useful. The fluorescence is dramatically enhanced when the metal-ion forms a chelate with appropriate organic ligands. An important property of these chelates is that the radiation is absorbed at a wavelength characteristic of the ligand and is emitted as a line spectrum characteristic of the metal-ion. This is due to an intramolecular energy transfer from the ligand to the central metal-ion (1 2). In general, it is difficult to predict theoretically which organic molecules-ligands can form highly fluorescent complexes with $Eu^{3+}$ and $Tb^{3+}$. Some classes of compounds i.e. the diketones, tetracyclines, phenanthrolines, acetylene derivatives, five-membered heterocyclic ring derivatives, benzoic acid derivatives, biphenyl derivatives, pyridine derivatives, pyrimidine and pyrazine derivatives, di- and tripyridyl derivatives, quinoline derivatives, aza-uracil and purine derivatives and phosphorimido-derivatives have been identified as fluorogenic ligands of $Eu^{3+}$ and/or $Tb^{3+}$ (13).

In time-resolved fluorometric immunoassays, it is desirable to use a chelate-label which can be detected down to the subpicomolar range (5). Alternatively, multiple labelling strategies can be used in order to achieve subpicomolar analyte sensitivity (1 and 4–16). More recently, there have been efforts to combine time-resolved fluorometric immunoassay with enzymatic catalysis. In one version of this approach, the primary immunological label is alkaline phosphatase (ALP); its acid (FSAP). The nonhydrolysed ester (FSAP) and the hydrolysed ester (FSA) have different behaviour in $Tb^{3+}$-EDTA solutions. When FSA is added to an aqueous alkaline solution containing $Tb^{3+}$-EDTA, a mixed complex is formed which emits long-lived fluorescence characteristic of $Tb^{3+}$. FSA is an appropriate ligand for energy transfer to the metal-ion. An intact hydroxyl group on the FSA molecule is essential for these highly fluorescent mixed complexes to be formed. FSAP does not form any fluorescent complexes with $Tb^{3+}$-EDTA. In a heterogeneous immunoassay design, ALP activity can be monitored with use of FSAP as substrate, by measuring the released FSA after adding an alkaline solution of $Tb^{3+}$-EDTA (17). This system has been used for the highly sensitive and rapid quantification of alpha-fetoprotein and thyrotropin in serum (18,19).

SUMMARY OF THE INVENTION

According to an aspect of the invention, fluorescent lanthanide metal chelates are selected from compounds of the following formulas I through XXXIII:

I

II

III

IV

V

VI

VII

VIII

IX

X

XI

XII

XIII

XIV

XV

XVI

XVII

XVIII

XIX

XX

According to another aspect of the invention, in a time resolved fluorescent based assay, the selected esters of chelates of formulas I through XXXIII are enzymatically treated to render the chelates either fluorescent or non-fluorescent when combined with a selected lanthanide metal.

BRIEF DESCRIPTION OF THE DRAWINGS

Preferred embodiments of the invention are discussed with respect to the following drawings wherein.

DETAILED DESCRIPTIONS OF THE PREFERRED EMBODIMENTS

Examination of this and other enzyme immunoassay systems reveals that immunological assays with sub-picomolar analyte sensitivity and speed can be developed if the substrate (i.e. FSA) can be quantified at a concentration level of ~$10^{-8}$M. The analyte detectability at levels <$10^{-12}$M is due to the enzymatic amplification introduced by ALP or other enzymes.

Thirty-three compounds which provide $Eu^{3+}$ and/or $Tb^{3+}$ fluorogenic chelators have been identified. These molecules have two criteria in common: (a) that their structure contains aromatic or heteroaromatic rings capable of absorbing electromagnetic radiation which internally excites the lanthanide and, (b) that the structure contains a lanthanide binding site which preferably but not necessarily consists of at least one carboxyl group and a hydroxyl group; the hydroxyl group being available for conversion to either a phosphate ester or a galactoside. These derivatives can also act as substrates for alkaline phosphatase or $\beta$-galactosidase, respectively.

The molecules are identified as follows in formulas I through XXXIII:

I

II

III

IV

V

VI

VII

VIII

IX

X

XI

XII

XIII

XIV

XV

XVI

XVII

-continued

XVIII

XIX

XX

XXI

XXII

XXIII

XXIV

XXV

XXVI

XXVII

-continued

XXVIII

XXIX

XXX

XXXI

XXXII

XXXIII

The registry numbers for these compounds is as follows: I, 3-hydroxyflavone, 577-85-5; II, 4-hydroxyquinoline-2-carboxylic acid, 492-27-3; III, 2-hydroxynicotinic acid, 609-71-2; IV, 1-hydroxy-2-naphthoic acid, 86-48-6; V, 5-fluorosalicyclic acid, 345-16-4; VI, 6-hydroxynicotinic acid, 5006-66-6; VII, 2-hydroxy-6-methylpyridine-3-carboxylic acid, 38116-61-9; VIII, 3-hydroxy-2-naphthoic acid, 92-70-6; IX, 3-hydroxypicolinic acid, 874-24-8; X, 2-hydroxy-5-nitrobenzoic acid, 96-97-9; XI, 4-hydroxy-7-trifluromethyl-3-quinoline carboxylic acid, 574-92-5; XII, 3-hydroxy-4,7,7-trimethylbicyclo [2.2.1] heptane-2-acetic acid, 81925-04-4; XIII, 4-hydroxy-7-methyl-1,8-naphthyridine-3-carboxylic acid, 13250-97-0; XIV, 3-hydroxy-2-quinoxaline carboxylic acid, 1204-75-7; XV, 3-hydroxy-2-(hydroxy-methyl) pyridine, 14173-30-9; XVI, 9-hydroxy-9-fluorene carboxylic acid, 467-69-6; XVII, 5-hydroxy-2-indole carboxylic acid, 21598-06-1; XVIII, 5-hydroxyindole-3-acetic acid, 54-16-0; XIX, 7-hydroxycoumarin-4-acetic acid, 6950-82-9; XX, 2-quinoxalinol, 1196-57-2-, XXI, 2,8-bis(trifluoromethyl)-4-quinolinol, 35853-41-9; XXII, 2,4-dihydroxypyrimidine-5-carboxylic acid, 23945-44-0; XXIII, 4,8-dihydroxyquinoline-2-carboxylic acid, 59-00-7; XXIV, 7-(trifluoromethyl)-4-qinolinol, 322-97-4; XXV, 2,4-quinolinediol, 86-95-3; XXVI, 7-hydroxy-4-methyl-coumarin, 90-33-5;

XXVII, 1,3-dihydroxy-9-acridine carboxylic acid, 28332-99-2; XXVIII, 3-quinolinecarboxylic acid, 6480-68-8; XXIX, calcein blue, 54375-47-2; XXX, 4-bromo-2,8-bis(trifluoromethyl) quinoline, 35853-45-3; XXXI, 2-quinoxaline carboxylic acid, 879-65-2; XXXII, Pterin-6-carboxylic acid, 948-60-7; XXXIII, 4-methylumbelliferyl phosphate, sodium salt, 22919-26-2.

Molecules IX, XI, XIII, XXIX and XXIII of the above formulae are good fluorogenic chelators for both $Eu^{3+}$ and $Tb^{3+}$ and molecules IX, XI, XIII, XIV, XXIX and XXXII of the above formulae are good fluorogenic chelators for $Eu^{3+}$ only. Under optimised measuring conditions of pH and presence or absence of EDTA, these chelators can be detected at levels $<10^{-8}M$. Thus, these substrates demonstrate utility in highly sensitive enzymatically amplified time-resolved fluorometric immunoassays. One chelator identified, 4-methylumbelliferyl phosphate of formula XXXIII, which is a substrate for alkaline phosphatase, was used as a model to develop new heterogeneous time-resolved fluorescence immunoassays for thyrotropin (TSH) and thyroxine (T4) in serum.

In order to demonstrate the fluorescent capabilities of the various chelators, the following experimental section is provided as a technical guide for investigating the fluorescent properties of preferred chelators.

Instrumentation

All time-resolved fluorometric measurements were carried out in white polystyrene microtiter wells obtained from Dynatech Laboratories, Alexandria, Va., using the 615 TM Immunoanalyzer. This instrument is a microsecond time-resolved fluorometer commercially available by CyberFluor Inc., Toronto, Canada. The emission filter used, at 615 nm, was found suitable for both $Eu^{3+}$ and $Tb^{3+}$, as previously described (18). The excitation source is a nitrogen laser providing excitation radiation at 337.1 nm. No effort was made to optimise the excitation wavelength for each chelator tested.

Chemicals and Solutions

The candidate organic chelators tested are shown in FIG. 1. All of them were obtained from Aldrich Chemical Co., Milwaukee, Wis. 53233. Calf intestine alkaline phosphatase (ALP) was obtained from Boehringer Mannheim Canada, Montreal PQ. Alkaline phosphatase-labelled streptavidin (SA-ALP) was obtained from Zymed Laboratories Inc., San Fransisco, Calif. 94080, as a 0.75 mg/mL solution. White, opaque 12-well polystyrene microtiter strips coated with monoclonal antithyrotropin antibody (for the TSH assay) or a thyroxine-globulin conjugate (for the T4 assay) were obtained from CyberFluor. The biotinylated detection antibodies, standards and buffers needed for the immunoassays were also from CyberFluor. Europium (III) chloride hexahydrate and terbium (III) chloride hexahydrate were from Aldrich. All other chemicals were from Sigma Chemical Co., St. Louis, Mo. 63178.

All chelators were dissolved in a 0.1 mol/L Tris buffer, pH 9.0, to prepare stock $10^{-3}$ mol/L solutions. More dilute solutions were prepared in the same buffer as needed. The alkaline phosphatase substrate buffer was a 0.1 mol/L Tris, pH 9.0, containing 0.1 mol/L NaCl and 1 mmol/L $MgCl_2$. The diluent for the biotinylated detection TSH antibody and the SA-ALP conjugate was a 6% (w/v) solution of bovine serum albumin (BSA) in a 50 mmol/L Tris buffer, pH 7.40, containing 0.5 g of sodium azide per liter. The wash solution was prepared by dissolving 9 g of NaCl and 0.5 mL of polyoxyethylenesorbltan monolaurate (Tween 20) in 1 liter of distilled water.

Procedures

All chelators were screened by mixing 100 μL of a chelator solution and 100 μL of a $Eu^{3+}$ or $Tb^{3+}$ solution, ($4 \times 10^{-3}$ mol/L in water) and measuring the delayed fluorescence on the 615 TM Immunoanalyzer. The chelators according to preferred embodiments of the invention were further tested with $Eu^{3+}$ or $Tb^{3+}$ solutions of various pH, in the absence or presence of EDTA. Calibration curves and detection limits were constructed or calculated by adding 100 μL of an aqueous $Eu^{3+}$ or $Tb^{3+}$ solution to 100 μL of a chelator solution in a 0.1 mol/L Tris buffer of pH 9.0. For the chelator according to formula V, we added 100 μL of a $Tb^{3+}$-EDTA solution, $10^{-3}$ mol/L in a 0.5 mol/L Tris buffer (18) of pH 12.5. For chelators of formula XI and XIII, we added 100 μL of a $4 \times 10^{-3}$ mol/L solution of $Eu^{3+}$ or $Tb^{3+}$ in a 0.1 mol/L Tris buffer, pH 11, containing $5 \times 10^{-3}$ mol/L EDTA.

Immunoassay of TSH

Pipet 100 μL of TSH standards (0, 0.25, 0.50, 1, 2, 4, 8, and 16 mU/L) into monoclonal antibody-coated wells and then add 50 μL of biotinylated monoclonal detection antibody diluted 50-fold in the 6% BSA diluent. Incubate with mechanical shaking for 1 h at room temperature and wash×4. Add 100 μL/well of the SA-ALP conjugate diluted 3000-fold in the 6% BSA diluent, incubate 15 min as above and wash×4. Add 100 μL/well of the 4-methylumbelliferyl phosphate substrate diluted to a concentration between $5 \times 10^{-6} - 5 \times 10^{-5}M$ in the alkaline phosphatase substrate diluent and incubate as above for 30 min. Then, add 1 00 mL of a $Eu^{3+}$ solution, $4 \times 10^{-3}M$ in water, mix and measure fluorescence within 5 min with the 615 TM Immunoanalyzer. The calibration curve and data reduction are carried out automatically by the analyzer.

Immunoassay of T4

Pipet 10 μL of thyroxine standards or serum samples into thyroxine-coated wells and then add 100 μL of biotinylated T4 antibody diluted 20-fold in the T4-antibody diluent. Incubate with mechanical shaking for 1 h at room temperature and wash×4. Add 100 μL/well of the SA-ALP conjugate and complete the assay as described for TSH but substrate incubation is only 15 min.

Results and Discussion Based on the Experimental Procedure

Many chelators of the formulae possess a hydroxyl group which could be converted to a phosphate ester or galactoside for the purpose of using them as substrates of alkaline phosphatase or μ-galactosidase as has already been reported for the chelator of formula V which is included for comparison (17-19). In some cases, sets of candidate chelators with only one group difference were tested i.e. chelators of formualae XIV, XX and XXXI, to demonstrate the importance of the different groups. Derivatives of a particular structure i.e. 4-methylumbelliferone (formulae XXVI, XIX, XXIX and XXXIII) and quinoline derivatives (formula II, XI, XXI, XXIII, XXIV, XXV, XXVIII, XXX) were tested. From the structures of the formulae ten compounds form highly fluorescent complexes with $Eu^{3+}$. Five of these chelators can also form fluorescent complexes with $Tb^{3+}$, as set out in following Table 1. Only the chelator of formula V was found to be unique for $Tb^{3+}$. Chelator XXIX was better, in terms of fluorescence intensity under the conditions of measurement, with $Tb^{3+}$ in comparison to $Eu^{3+}$. Two chelators, XI and XIII exhibited the property of working in the presence of excess EDTA i.e. they form fluorescent complexes with $Eu^{3+}$ and $Tb^{3+}$ chelated to EDTA. This property is also seen with chelator V (previously reported). In all other cases, fluorescence of the complexes decreases dramatically in the presence of EDTA. For all the chelators, the fluorescence measured is long-lived and lanthanide-specific. Native chelator fluorescence may also exist but is not detected by the time-resolved fluorometer.

Fluorescence intensity of the complexes varies with pH as shown in Table 1. However, solutions of $Eu^{3+}$ and $Tb^{3+}$ in buffers of alkaline pH deteriorate quickly due to hydroxide precipitation. For this purpose, complexes are preferably formed with the addition of an aqueous solution of $Eu^{3+}$ or $Tb^{3+}$ (pH~6.5) which is stable for long periods of time at room temperature. In the cases of chelators V, XI and XIII, the $Eu^{3+}$ and $Tb^{3+}$ solutions were made in the presence of excess EDTA at pH 12.5 (for formula V) or 11; respectively. These solutions were also very stable when stored at room temperature. The fluorescence intensity of the complexes was highest when the $Eu^{3+}$ and $Tb^{3+}$ concentration in the final solution was around $2 \times 10^{-3}$ mol/L. Lower concentrations resulted in lower fluorescence signals.

The stability of fluorescence intensity with time was studied. Fluorescence intensity remained stable ($\pm 10\%$) for at least 3 h in the case of chelators IX, XI, XIII, XIV, XXIX and XXXII and $Eu^{3+}$ and/or $Tb^{3+}$.

Fluorescence intensity decreased with time (change $\geq 10\%$ per hour) in the case of chelators II, XIX, XXXI and XXXIII. This decrease was also noticed for chelator V and previously reported (18).

Calibration curves with all chelators that form highly fluorescent complexes with $Eu^{3+}$ and/or $Tb^{3+}$ were constructed and the detection limits were calculated as the concentration that could be distinguished from zero with 95% confidence. The detection limits are reported in Table 1. Representative calibration curves are shown in FIG. 1. In all cases but one, detection limits were $<10^{-8}$ mol/L. Some chelators were clearly superior to V chelators in terms of detectability. Chelator (V) has already been used as a phosphate ester to devise highly sensitive immunoassays (18,19).

The modification of the structures of these chelators i.e. tranformation into phosphate esters or galactosides can provide desired spectroscopic changes and/or chelation changes and/or energy transfer changes, the net result being an increase or loss of fluorescence in the presence of the lanthanides depending on the desired effect. It is also understood that substitution of various entities of the compounds of formulae I to XXIII may be done to enhance performance. Such substitutions may be with existing radicals or at other positions about the ringed structure. Such substition may be in regard to other halogen groups, other alkyl groups and other alkylene groups and the like.

Another interesting application of the invention is to have a pair of compounds A and B one of which, A, is an enzyme substrate that forms fluorescent complexes with $Eu^{3+}$ or $Tb^{3+}$. Upon enzymatic cleavage of a group from A, which is then transformed to B, the ability of A to form fluorescent complexes is lost. One such pair reported here for the first time is XXXIII and XXVI. Only XXXIII forms long-lived, highly fluorescent complexes with $Eu^{3+}$.

Figure 1A:
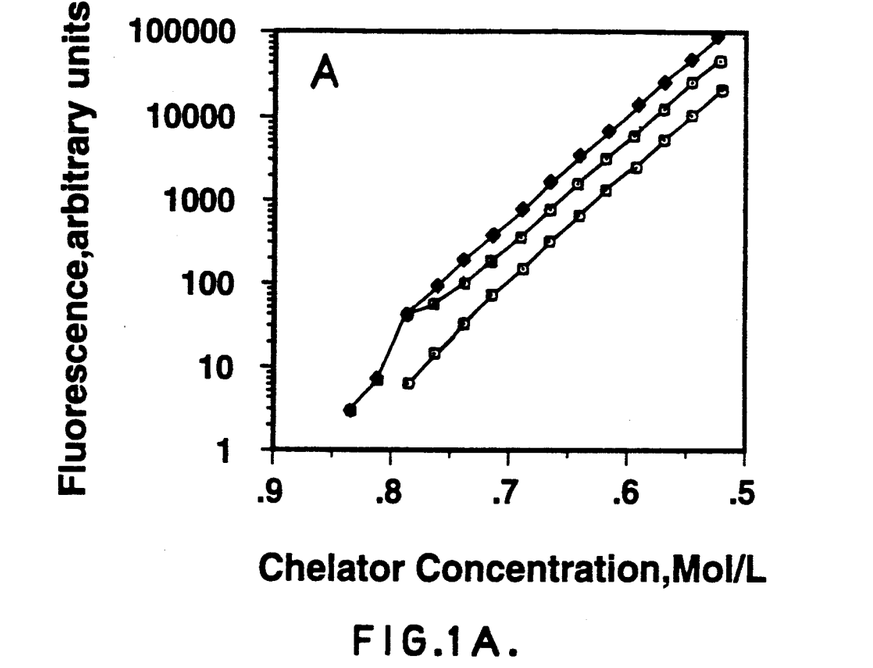
FIG. 1 Logarithmic plots of fluorescence vs concentration of candidate fluorogenic lanthanide chelator. In all cases A to E but D, the fluorescence of each Eu3+ chelate was higher or equal (C) to the corresponding fluorescence of the Tb3+ chelate; the Eu3+-chelate fluorescence curve in plots A to E is thus on top of the Tb3+-chelate fluorescence curve, except in case D. The chelators represented are XI (A, the third curve representing the lowest fluorescence is due to the Tb3+-EDTA-fluorosalicylate complex as described in (17); XIII (B); IX (C); XXIX (D); XXXIII (E); II (F, with Eu3+); XIV (G, with Eu3+); XIX (H, with Eu3+); XXXI (I, lower curve with Eu3+); XXXII (I, upper curve with Eu3+).
Figure 1B:
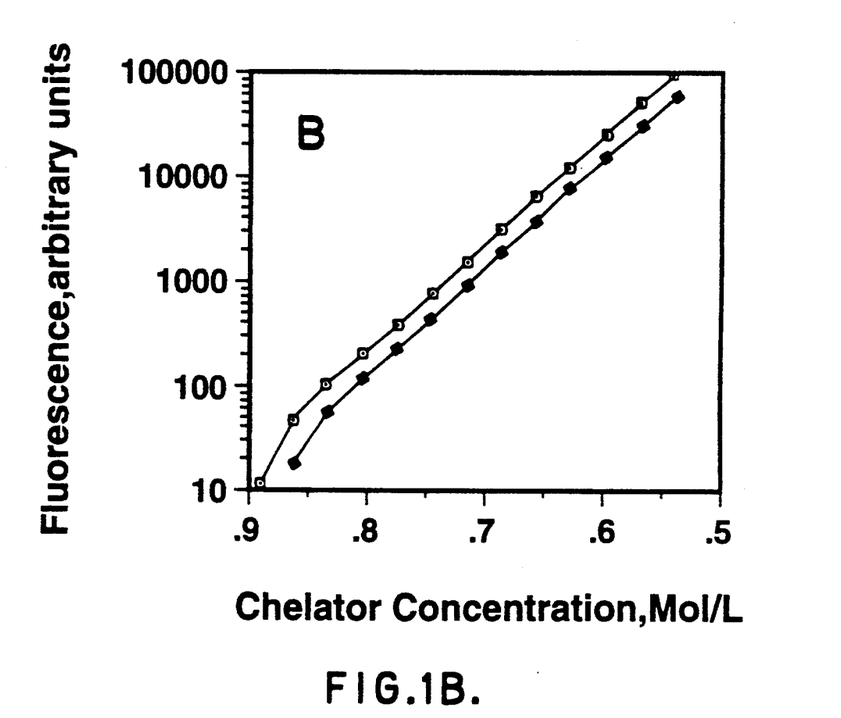
Figure 1C:
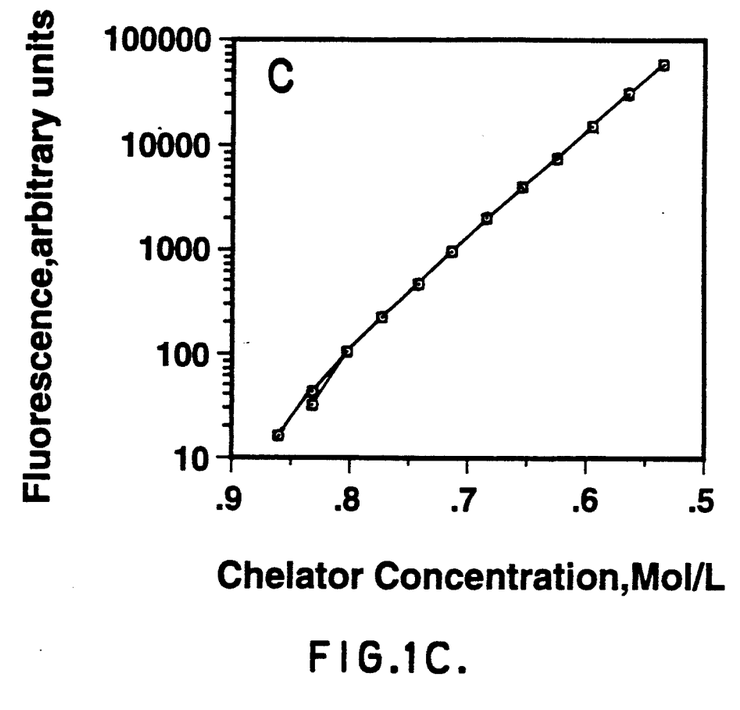
Figure 1D:
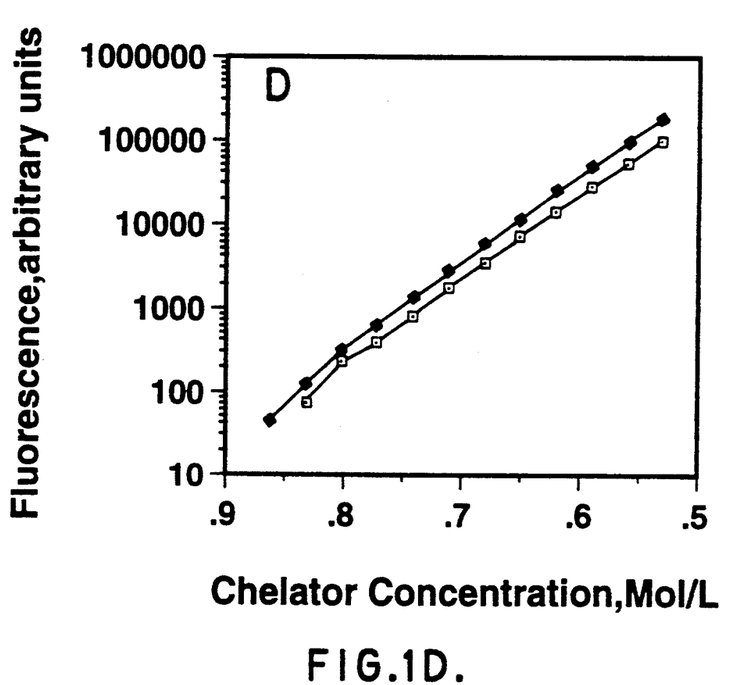
Figure 1E:
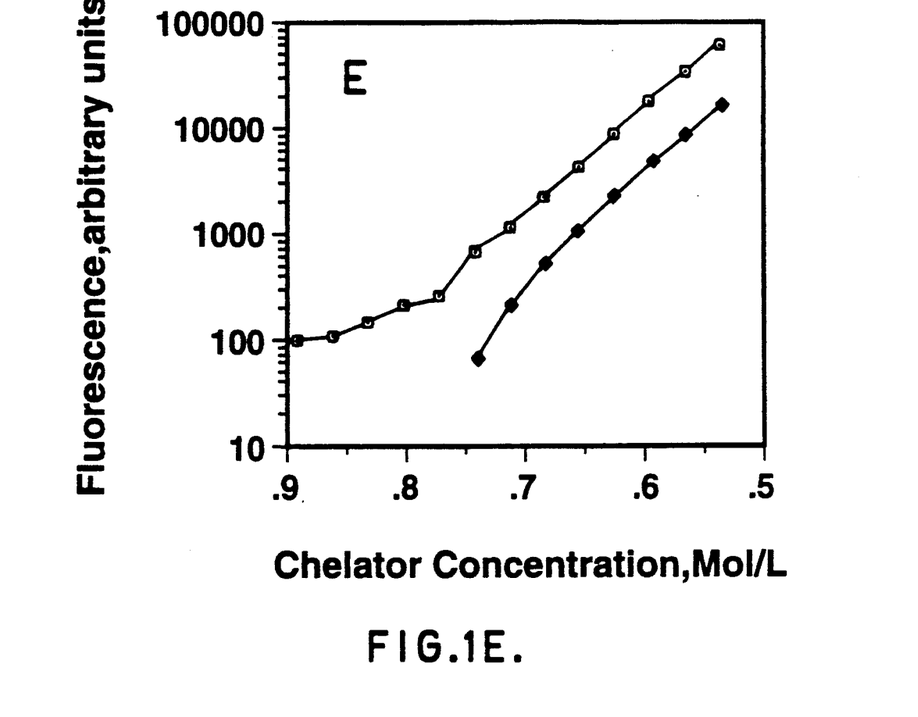
Figure 1F:
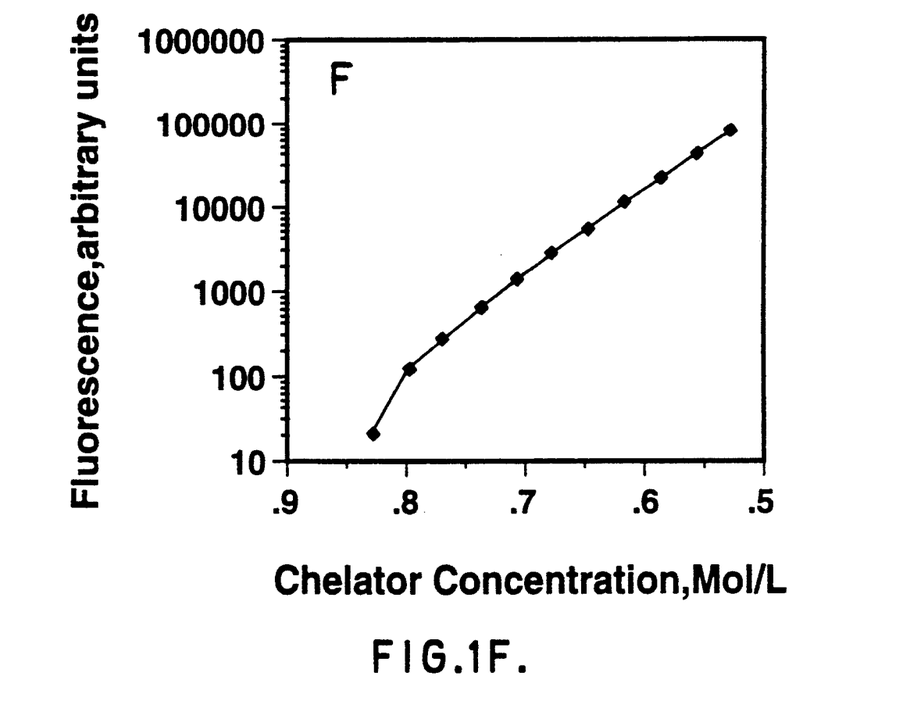
Figure 1G:
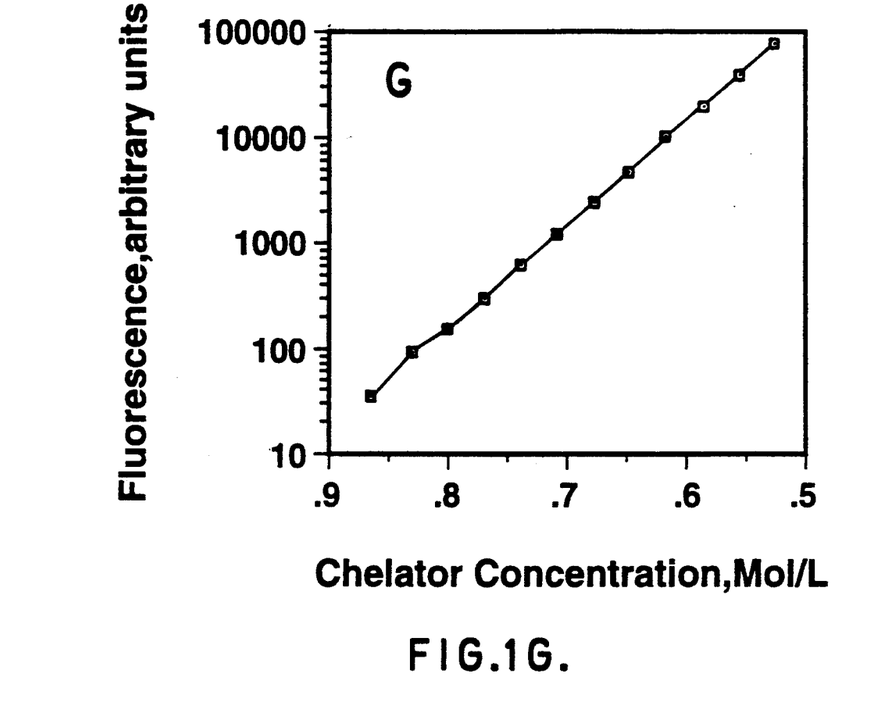
Figure 1H:
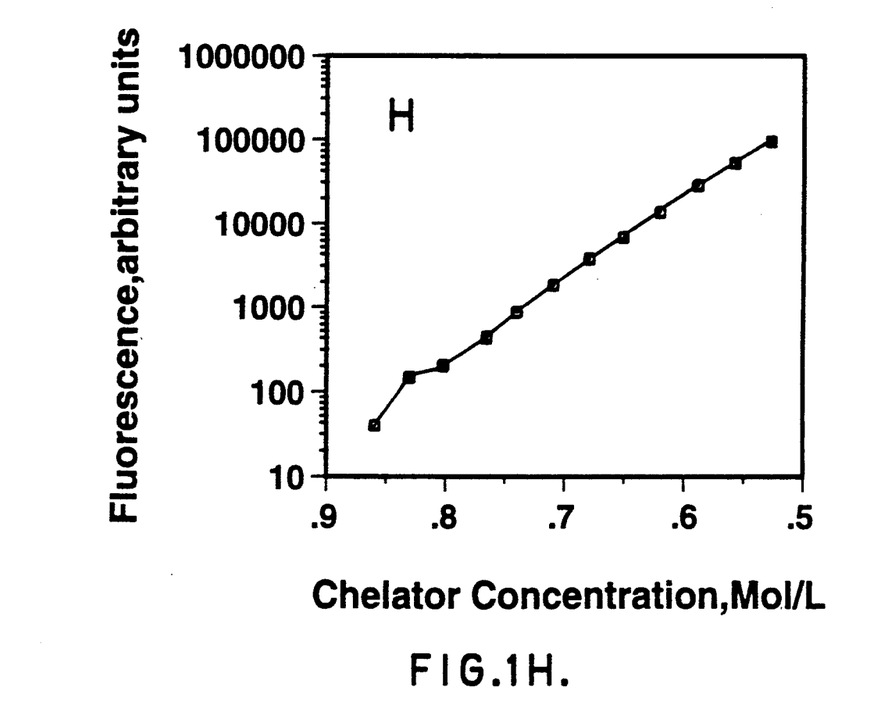
Figure 1I:
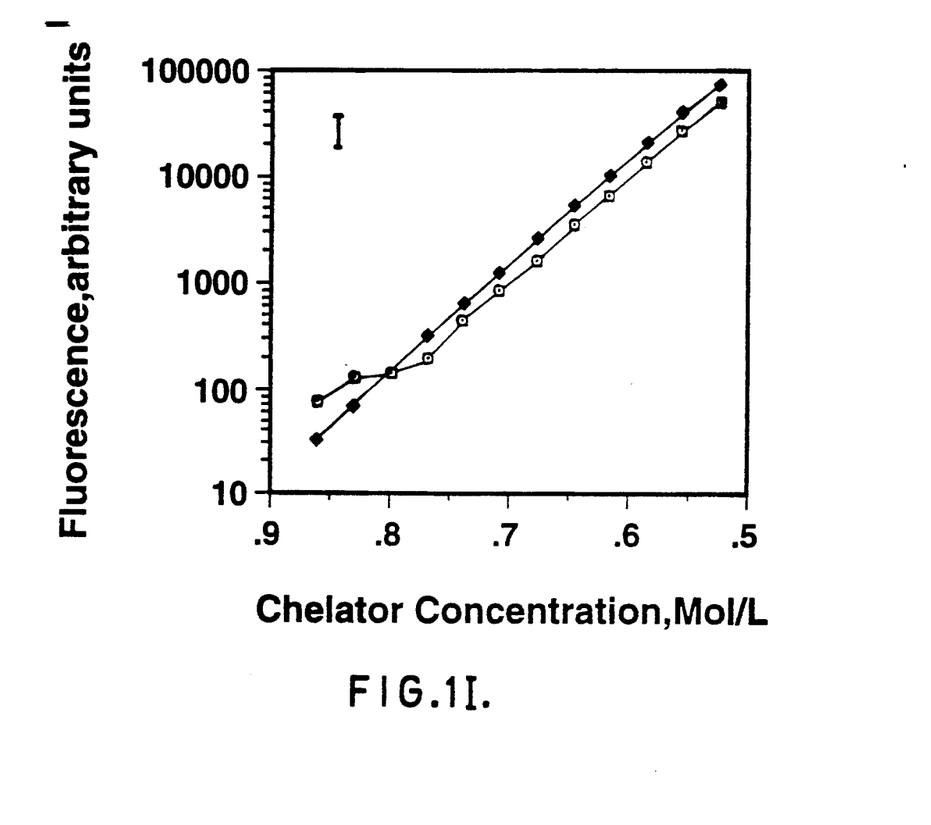
Figure 2A:
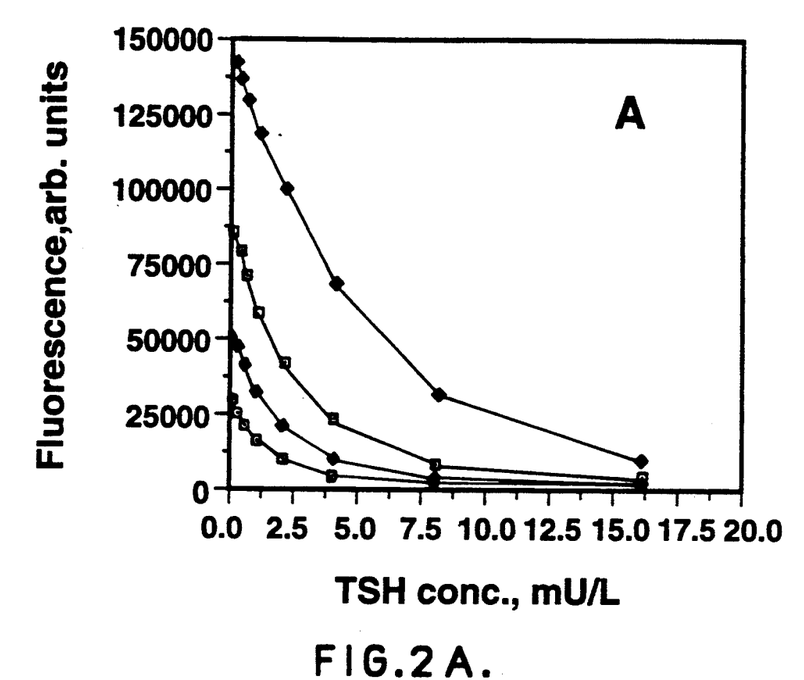
FIG. 2 Calibration curves for the proposed TSH assay (A). Fluorescence vs TSH concentration on linear axes (B). A percentage plot, where Bo is the fluorescence of the zero standard and B the fluorescence of all other standards. The concentration of the substrate used was (in mol/L from bottom to top): $5 \times 10^{-6}$; $1 \times 10^{-5}$; $2 \times 10^{-5}$; $5 \times 10^{-5}$.
Figure 2B:
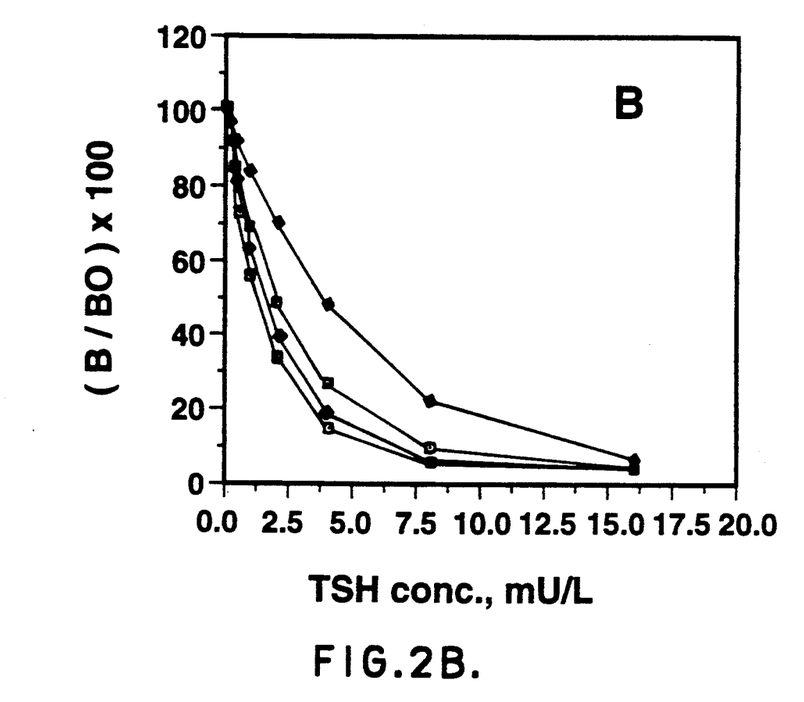

When ALP cleaves-off phosphate to produce XXVI, the latter does not exhibit long-lived fluorescence in the presence of $Eu^{3+}$. Classically, XXXIII is a non-fluorescent ALP substrate; when ALP cleaves-off phosphate, the product, XXVI, exhibits blue, short-lived fluorescence. The pair XXXIII, XXVI and $Eu^{3+}$ were used to develop two model time-resolved fluorometric immunoassays for TSH and T4 in serum. The design of the TSH assay is of the non-competitive heterogeneous immunoassay format where an immunocomplex of the type solid-phase-coating antibody-TSH-detection antibody-biotin-streptavidin-alkaline phosphatase, is formed in polystyrene microtiter wells. The activity of ALP can then be measured in a number of different conventional ways. In this work, we detected ALP by adding the substrate XXXIII for 30 min, followed by addition of a $4 \times 10^{-3}$ mol/L $Eu^{3+}$ solution to form the fluorescent complex with the unreacted substrate. The calibration curves obtained are shown in FIG. 2. The sensitivity and range of assay can be adjusted by adjusting the concentration of the substrate added.

It is important to note that by this particular selection of substrates, the shape of the calibration curve with this substrate, is unique for this type of assay. Usually, the more the analyte in the sample, the more the signal observed; thus, cal. curves show proportionality between analyte concentration and signal. In the system of this invention, there is an inverse relationship between TSH concentration and signal, as shown in FIG. 2. This is due to the fact that the more the ALP present in the immunocomplex, the less the signal observed with the proposed substrate. The detection limit of the TSH assay is about 0.1 mU/L. Precision of this particular embodiment was excellent at 2-3% within the measuring range.

In comparison to conventional systems, it is possible to use the above principle for the 'competitive-type' heterogeneous assay formats which traditionally have calibration curves of the shape shown in FIG. 2 i.e. there is an inverse relationship between analyte concentration and signal. In the system according to an embodiment of this invention, the curves would show proportionality between analyte concentration and signal because high alkaline phosphatase concentration is associated with low signal.

Figure 3A:
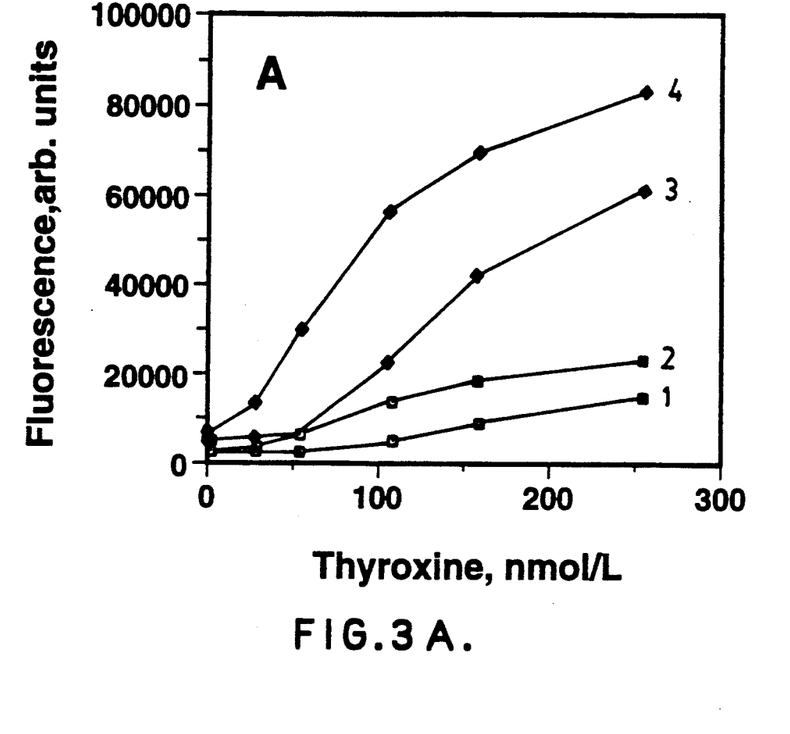
FIG. 3 Calibration curves for the proposed thyroxine assay (A). Double linear plots. (B) Double logarithmic plots. The substrate concentration and antibody dilutions used were: $5 \times 10^{-6}$M and 10-fold (1); $5 \times 10^{-6}$M and 20-fold (2); $2 \times 10^{-5}$M and 10-fold (3); $2 \times 10^{-5}$M and 20-fold (4).
Figure 3B:
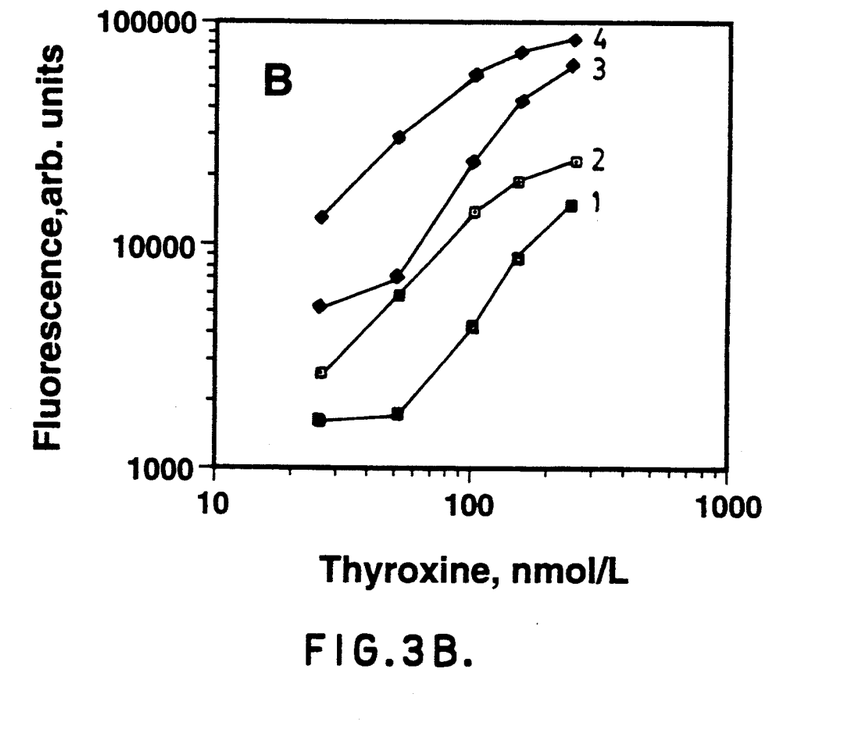
Figure 4:
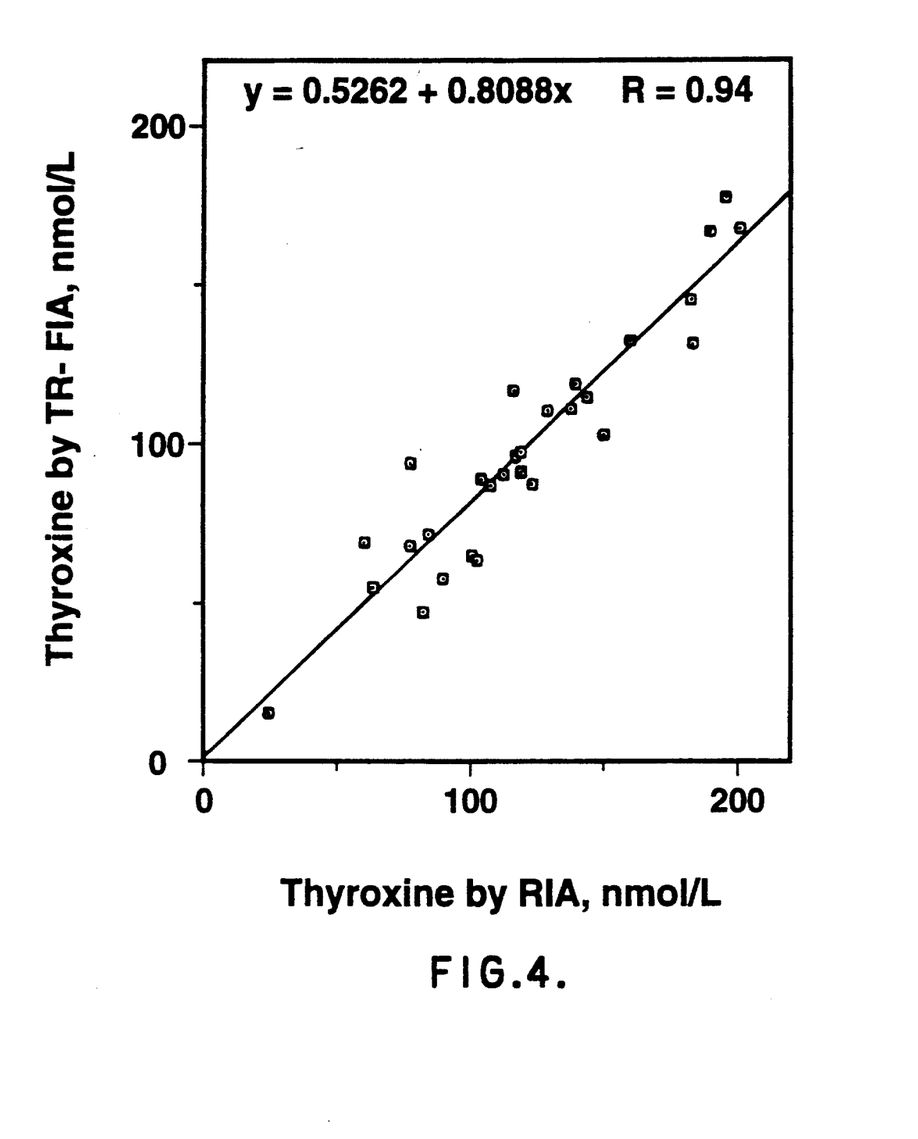
FIG. 4 Correlation between serum thyroxine results obtained with a radioimmunoassay (RIA) and the proposed assay method (TR-FIA).

To demonstrate this, a competitive assay for T4 was designed as follows: Polystyrene microtiter wells were coated with a T4-protein conjugate as described previously (20). In the assay, T4 in the sample competes with immobilized T4 for binding to a biotinylated anti-T4 monclonal antibody. After washing out excess reagents, we added a SA-ALP conjugate to form the immunocomplex: solid-phase-T4-antibodybiotin-SA-ALP. The activity of ALP can then be quantified with use of the substrate, XXXIII. With a conventional detection system, the amount of signal generated by ALP is inversely related to the analyte concentration and the calibration curves have a shape similar to those of FIG. 2. In this alternative system, there is a direct relationship between signal and analyte concentration. Calibration curves obtained with the system are shown in FIG. 3. Sensitivity can be adjusted by changing the antibody dilution, the substrate concentration and the substrate incubation time. Under optimised conditions, 30 clinical samples have been analyzed by the method of this invention and by a conventional radioimmunoassay procedure. The comparison is shown in FIG. 4. A good correlation exists between the two methods. Adiditonally, precision studies with three samples gave the following results (N=12): T4 of 112 nmol/L, CV=8.1%; 59 nmol/L, CV 6.2%; 25.9 nmol/L, 8.2%. Samples diluted 2-fold or 4-fold gave values between 93–105% of expected results confirming a good linearity of the proposed procedure.

Enzymatically amplified time-resolved fluorescence immunoassays exhibit excellent sensitivity and can be used for the routine manual or automated assay of many analytes in biological fluids. The first system reported, is based on alkaline phosphatase and the substrate 5-fluorosalicyl phosphate (FSAP) in combination with $Tb^{3+}$ (17–19). Other possible chelators can be used which offer better detectability in comparison to FSA. Moreover, some of these chelators form stable complexes with $Eu^{3+}$ and $Tb^{3+}$ thus being advantageous to the previously reported system in which fluorescence decays with time.

A unique system based on the pair 4-methylumbilliferyl phosphate (4-MUP) of formula XXXIII and 4-methylumbelliferone (4-MU) of formula XXVI in combination with $Eu^{3+}$ has been demonstrated. This pair works in the exact opposite way in comparison to the reported FSAP-FSA-$Tb^{3+}$ system (1 7–19). Here, 4-MUP forms the fluorescent complex with $Eu^{3+}$ cleavage of phosphate by alkaline phosphatase releases 4-MU which does not form fluorescent complexes with $Eu^{3+}$. This system works well in both 'non-competitive-type' and 'competitive-type' immunoassays. Its advantage in comparison to the conventional methodologies is mainly in competitive-type assays in which the calibration curve shows a direct relationship between analyte concentration and signal. In this case, assay sensitivity is superior because of the much larger signal ratios obtained between the first two standard points of the calibration curve. This system can thus be used in combination with the previously described system (17–19) to devise immunoassays that show a direct relationship between signal and analyte concentration irrespective of the immunoassay type used (competitive or non-competitive).

Although preferred embodiments of the invention are described herein in detail, it will be understood by those skilled in the art that variations may be made thereto without departing from the spirit of the invention or the scope of the appended claims.

TABLE 1

Optimal Assay Conditions of Chelators in the Presence of $Eu^{3+}$ or $TB^{3+}$

| Europium Chelator | Works in presence of EDTA? | Detection Limit, Mol/L | Stability of Fluorescence | pH optimum[2] |
|---|---|---|---|---|
| II | No | $5 \times 10^{-9}$ | Poor | 11 |
| IX | No | $5 \times 10^{-9}$ | Good | 9-11 |
| XI | Yes | $2 \times 10^{-9}$[1] | Good[1] | 11[1] |
| XIII | Yes | $2 \times 10^{-9}$[1] | Good[1] | 11[1] |
| XIV | No | $2.5 \times 10^{-9}$ | Good | 11 |
| XIX | No | $2.5 \times 10^{-9}$ | Poor | 9-11 |
| XXIX | No | $4 \times 10^{-9}$ | Good | 9-11 |
| XXXI | No | $7 \times 10^{-9}$ | Poor | 11 |
| XXXII | No | $2.5 \times 10^{-9}$ | Good | 9-11 |
| XXXIII | No | $2.5 \times 10^{-9}$ | Poor | 9-11 |
| Terbium Chelator | | | | |
| V | Yes | $5 \times 10^{-9}$[1] | Poor[1] | 12..5[1] |
| IX | No | $5 \times 10^{-9}$ | Good | 11 |
| XI | Yes | $3 \times 10^{-9}$[1] | Good[1] | 11[1] |
| XIII | Yes | $5 \times 10^{-9}$[1] | Good[1] | 11[1] |
| XIX | No | $2 \times 10^{-9}$ | Good | 11 |
| XXXIII | No | $3.9 \times 10^{-8}$ | Poor | 11 |

[1]Studies done in the presence of $Eu^{3+}$ or $Tb^{3+}$ and EDTA
[2]Solutions of $Eu^{3+}$ and $Tb^{3+}$ are stable at alkaline pH only in the presence of excess EDTA. Detection limits were thus established at optimal pH only for chelators V, XI and XIII. In all other cases, aqueous solutions of $Eu^{3+}$ and $Tb^{3+}$ of pH 6.5 were used as described under procedures.

We claim:
1. Fluorescent lanthanide metal chelator selected from compounds of the following formulas:

2. Fluorescent chelator of claim 1 for europium and terbium.
3. Fluorescent chelators of claim 2 for europium selected from compounds of the formulas II and XI.
4. Fluorescent chelators of claim 2 for terbium of the formula XI.

* * * * *